(12) United States Patent
Wiley, II et al.

(10) Patent No.: US 8,630,873 B1
(45) Date of Patent: Jan. 14, 2014

(54) SYSTEMS AND METHODS FOR SHIFTING PRESCRIPTION MARKET SHARE BY PRESENTING PRICING DIFFERENTIALS FOR THERAPEUTIC ALTERNATIVES

(75) Inventors: Joseph Lee Wiley, II, Douglasville, GA (US); Kenneth E. Burkett, Southlake, TX (US)

(73) Assignee: NDCHealth Corporation, Atlanta, GA (US)

( * ) Notice: Subject to any disclaimer, the term of this patent is extended or adjusted under 35 U.S.C. 154(b) by 0 days.

(21) Appl. No.: 13/435,255

(22) Filed: Mar. 30, 2012

Related U.S. Application Data

(62) Division of application No. 11/608,068, filed on Dec. 7, 2006.

(60) Provisional application No. 60/748,432, filed on Dec. 8, 2005.

(51) Int. Cl.
*G06Q 10/00* (2012.01)
*G06Q 50/00* (2012.01)

(52) U.S. Cl.
USPC ..................................... 705/2; 705/3; 705/20

(58) Field of Classification Search
USPC ....................................................... 705/2, 20
See application file for complete search history.

(56) References Cited

U.S. PATENT DOCUMENTS

| | | |
|---|---|---|
| 4,674,041 A | 6/1987 | Lemon et al. |
| 4,723,212 A | 2/1988 | Mindrum et al. |
| 4,910,672 A | 3/1990 | Off et al. |
| 5,007,641 A | 4/1991 | Seidman |
| 5,080,364 A | 1/1992 | Seidman |
| 5,173,851 A | 12/1992 | Off et al. |
| 5,201,010 A | 4/1993 | Deaton et al. |
| 5,235,702 A | 8/1993 | Miller |
| 5,237,620 A | 8/1993 | Deaton et al. |
| 5,301,105 A | 4/1994 | Cummings |

(Continued)

FOREIGN PATENT DOCUMENTS

| | | |
|---|---|---|
| CA | 2482370 A1 | 3/2006 |
| EP | 1310895 A2 | 11/2002 |

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Michael Fuelling
(74) *Attorney, Agent, or Firm* — Sutherland Asbill & Brennan LLP

(57) ABSTRACT

While a pharmacist may know of other medications approved by the FDA for the same medical condition, the pharmacist typically does not know what the therapeutically equivalent dose of those products is when compared to the originally prescribed item. In addition to this lack of equivalent dosage information, the pharmacist also is unable to determine if any of those other FDA approved items will save the consumer any money. Accordingly, embodiments of the invention can provide pharmacists and/or consumers with equivalent dosage information as well as pricing information for the equivalent dosage. Accordingly, based at least in part on this information, consumers may have an incentive to and may decide to purchase to another prescription drug, thereby shifting market share to a preferred prescription drug or pharmaceutical manufacturer or provider.

1 Claim, 9 Drawing Sheets

(56) References Cited

U.S. PATENT DOCUMENTS

| | | | |
|---|---|---|---|
| 5,305,196 A | 4/1994 | Deaton et al. | |
| 5,327,508 A | 7/1994 | Deaton et al. | |
| 5,359,509 A | 10/1994 | Little et al. | |
| 5,388,165 A | 2/1995 | Deaton et al. | |
| 5,430,644 A | 7/1995 | Deaton et al. | |
| 5,448,471 A | 9/1995 | Deaton et al. | |
| 5,544,044 A | 8/1996 | Leatherman | |
| 5,550,734 A | 8/1996 | Tarter et al. | |
| 5,588,649 A | 12/1996 | Blumberg et al. | |
| 5,592,560 A | 1/1997 | Deaton et al. | |
| 5,612,868 A | 3/1997 | Off et al. | |
| 5,621,812 A | 4/1997 | Deaton et al. | |
| 5,628,530 A | 5/1997 | Thornton | |
| 5,638,457 A | 6/1997 | Deaton et al. | |
| 5,642,485 A | 6/1997 | Deaton et al. | |
| 5,644,723 A | 7/1997 | Deaton et al. | |
| 5,644,778 A | 7/1997 | Burks et al. | |
| 5,649,114 A | 7/1997 | Deaton et al. | |
| 5,659,469 A | 8/1997 | Deaton et al. | |
| 5,675,662 A | 10/1997 | Deaton et al. | |
| 5,687,322 A | 11/1997 | Deaton et al. | |
| 5,704,044 A | 12/1997 | Tarter et al. | |
| 5,748,907 A | 5/1998 | Crane | |
| 5,749,907 A | 5/1998 | Mann | |
| 5,832,447 A | 11/1998 | Rieker et al. | |
| 5,832,457 A | 11/1998 | O'Brien | |
| 5,845,255 A * | 12/1998 | Mayaud | 705/3 |
| 5,857,175 A | 1/1999 | Day et al. | |
| 5,892,827 A | 4/1999 | Beach et al. | |
| 5,892,900 A | 4/1999 | Ginter et al. | |
| 5,915,007 A | 6/1999 | Klapka | |
| 5,926,795 A | 7/1999 | Williams | |
| 5,950,169 A | 9/1999 | Borghesi et al. | |
| 5,956,736 A | 9/1999 | Hanson et al. | |
| 5,963,915 A | 10/1999 | Kirsch | |
| 5,970,469 A | 10/1999 | Scroggie et al. | |
| 5,974,399 A | 10/1999 | Giuliani et al. | |
| 5,991,750 A | 11/1999 | Watson | |
| 6,000,828 A | 12/1999 | Leet | |
| 6,006,242 A | 12/1999 | Poole et al. | |
| 6,012,035 A | 1/2000 | Freeman, Jr. et al. | |
| 6,014,634 A | 1/2000 | Scroggie et al. | |
| 6,021,392 A | 2/2000 | Lester et al. | |
| 6,026,370 A | 2/2000 | Jermyn | |
| 6,041,309 A | 3/2000 | Laor | |
| 6,055,573 A | 4/2000 | Gardenswartz et al. | |
| 6,067,069 A | 5/2000 | Krause | |
| 6,067,524 A | 5/2000 | Byerly et al. | |
| 6,073,104 A | 6/2000 | Field | |
| 6,185,541 B1 | 2/2001 | Scroggie et al. | |
| 6,195,612 B1 | 2/2001 | Pack-Harris | |
| 6,202,923 B1 | 3/2001 | Boyer et al. | |
| 6,205,455 B1 | 3/2001 | Umen | |
| 6,208,973 B1 | 3/2001 | Boyer et al. | |
| 6,224,387 B1 | 5/2001 | Jones | |
| 6,240,394 B1 | 5/2001 | Uecker | |
| 6,260,758 B1 | 7/2001 | Blumberg | |
| 6,278,979 B1 | 8/2001 | Williams | |
| 6,282,516 B1 | 8/2001 | Giuliani | |
| 6,298,330 B1 | 10/2001 | Gardenswartz et al. | |
| 6,304,849 B1 | 10/2001 | Uecker et al. | |
| 6,307,940 B1 | 10/2001 | Yamamoto et al. | |
| 6,307,958 B1 | 10/2001 | Deaton et al. | |
| 6,321,210 B1 | 11/2001 | O'Brien et al. | |
| 6,324,516 B1 | 11/2001 | Shults et al. | |
| 6,330,546 B1 | 12/2001 | Gopinathan et al. | |
| 6,334,108 B1 | 12/2001 | Deaton et al. | |
| 6,341,265 B1 | 1/2002 | Provost et al. | |
| 6,343,271 B1 | 1/2002 | Peterson et al. | |
| 6,351,735 B1 | 2/2002 | Deaton et al. | |
| 6,377,935 B1 | 4/2002 | Deaton et al. | |
| 6,424,949 B1 | 7/2002 | Deaton et al. | |
| 6,427,020 B1 | 7/2002 | Rhoads | |
| 6,484,146 B2 | 11/2002 | Day et al. | |
| 6,542,902 B2 | 4/2003 | Dulond et al. | |
| 6,584,448 B1 | 6/2003 | Laor | |
| 6,632,251 B1 | 10/2003 | Rutten et al. | |
| 6,671,692 B1 | 12/2003 | Marpe et al. | |
| 6,671,693 B1 | 12/2003 | Marpe et al. | |
| 6,684,195 B1 | 1/2004 | Deaton et al. | |
| 6,714,918 B2 | 3/2004 | Hillmer et al. | |
| 6,757,898 B1 | 6/2004 | Ilsen et al. | |
| 6,769,228 B1 | 8/2004 | Mahar | |
| 6,795,809 B2 | 9/2004 | O'Brien et al. | |
| 6,859,780 B1 | 2/2005 | Cunningham | |
| 6,879,959 B1 | 4/2005 | Chapman et al. | |
| 6,885,994 B1 | 4/2005 | Scroggie et al. | |
| 7,013,284 B2 | 3/2006 | Guyan et al. | |
| 7,024,374 B1 | 4/2006 | Day et al. | |
| 7,058,584 B2 | 6/2006 | Kosinski et al. | |
| 7,058,591 B2 | 6/2006 | Giuliani et al. | |
| 7,111,173 B1 | 9/2006 | Scheidt | |
| 7,155,397 B2 | 12/2006 | Alexander et al. | |
| 7,225,052 B2 | 5/2007 | Foote et al. | |
| 7,228,285 B2 | 6/2007 | Hull et al. | |
| 7,233,913 B2 | 6/2007 | Scroggie et al. | |
| 7,309,001 B2 | 12/2007 | Banfield et al. | |
| 7,356,460 B1 | 4/2008 | Kennedy et al. | |
| 7,380,707 B1 | 6/2008 | Fredman | |
| 7,401,027 B2 | 7/2008 | Moore et al. | |
| 7,415,426 B2 | 8/2008 | Williams et al. | |
| 7,418,400 B1 | 8/2008 | Lorenz | |
| 7,426,480 B2 | 9/2008 | Granger et al. | |
| 7,597,247 B2 | 10/2009 | Helmin et al. | |
| 8,019,619 B2 | 9/2011 | Ghouri | |
| 8,046,242 B1 | 10/2011 | daCosta et al. | |
| 8,099,339 B1 | 1/2012 | Pinsonneault et al. | |
| 8,321,283 B2 | 11/2012 | Rowe, III et al. | |
| 2001/0001014 A1 | 5/2001 | Akins, III et al. | |
| 2001/0032099 A1 | 10/2001 | Joao | |
| 2001/0037216 A1 * | 11/2001 | Oscar et al. | 705/2 |
| 2001/0037224 A1 | 11/2001 | Eldridge et al. | |
| 2001/0041993 A1 | 11/2001 | Campbell | |
| 2002/0002495 A1 | 1/2002 | Ullman | |
| 2002/0035488 A1 | 3/2002 | Aquila et al. | |
| 2002/0044043 A1 | 4/2002 | Chaco et al. | |
| 2002/0049617 A1 | 4/2002 | Lencki et al. | |
| 2002/0055856 A1 | 5/2002 | Adams | |
| 2002/0065687 A1 | 5/2002 | Onoue | |
| 2002/0087554 A1 | 7/2002 | Seelinger | |
| 2002/0087583 A1 | 7/2002 | Morgan et al. | |
| 2002/0111832 A1 * | 8/2002 | Judge | 705/3 |
| 2002/0120473 A1 | 8/2002 | Wiggins | |
| 2002/0128883 A1 | 9/2002 | Harris | |
| 2002/0133503 A1 | 9/2002 | Amar et al. | |
| 2002/0138593 A1 | 9/2002 | Novak et al. | |
| 2002/0175370 A1 | 11/2002 | Bockelman | |
| 2002/0183979 A1 | 12/2002 | Wildman | |
| 2002/0198831 A1 | 12/2002 | Patricelli et al. | |
| 2003/0009357 A1 | 1/2003 | Pish | |
| 2003/0009367 A1 | 1/2003 | Morrison | |
| 2003/0028404 A1 | 2/2003 | Herron et al. | |
| 2003/0050799 A1 | 3/2003 | Jay et al. | |
| 2003/0074218 A1 | 4/2003 | Liff et al. | |
| 2003/0074222 A1 | 4/2003 | Rosow et al. | |
| 2003/0083903 A1 | 5/2003 | Myers | |
| 2003/0120588 A1 | 6/2003 | Dodd et al. | |
| 2003/0125986 A1 | 7/2003 | Collosi | |
| 2003/0149594 A1 | 8/2003 | Beazley et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0006490 A1 | 1/2004 | Gingrich et al. | |
| 2004/0019464 A1 | 1/2004 | Martucci et al. | |
| 2004/0039599 A1 * | 2/2004 | Fralic | 705/2 |
| 2004/0046020 A1 | 3/2004 | Andreasson et al. | |
| 2004/0049422 A1 | 3/2004 | Mortimer | |
| 2004/0054657 A1 | 3/2004 | Takeyama | |
| 2004/0073457 A1 * | 4/2004 | Kalies | 705/2 |
| 2004/0078234 A1 | 4/2004 | Tallal, Jr. | |
| 2004/0093242 A1 | 5/2004 | Cadigan et al. | |
| 2004/0107117 A1 | 6/2004 | Denny | |
| 2004/0111277 A1 | 6/2004 | Pearson et al. | |
| 2004/0111291 A1 | 6/2004 | Dust et al. | |

(56) References Cited

U.S. PATENT DOCUMENTS

| | | | |
|---|---|---|---|
| 2004/0117323 A1* | 6/2004 | Mindala | 705/400 |
| 2004/0138921 A1 | 7/2004 | Broussard et al. | |
| 2004/0148198 A1 | 7/2004 | Kalies | |
| 2004/0153336 A1 | 8/2004 | Virdee et al. | |
| 2004/0172281 A1 | 9/2004 | Stanners | |
| 2004/0188998 A1 | 9/2004 | Henthorn | |
| 2004/0249745 A1 | 12/2004 | Baaren | |
| 2005/0015280 A1 | 1/2005 | Gabel et al. | |
| 2005/0033604 A1 | 2/2005 | Hogan | |
| 2005/0033610 A1 | 2/2005 | Cunningham | |
| 2005/0060201 A1 | 3/2005 | Connely, III et al. | |
| 2005/0065821 A1* | 3/2005 | Kalies, Jr. | 705/2 |
| 2005/0086081 A1 | 4/2005 | Brock-Fisher | |
| 2005/0090425 A1 | 4/2005 | Reardan et al. | |
| 2005/0102169 A1 | 5/2005 | Wilson | |
| 2005/0125292 A1 | 6/2005 | Kassab et al. | |
| 2005/0154627 A1 | 7/2005 | Zuzek et al. | |
| 2005/0171815 A1 | 8/2005 | Vanderveen | |
| 2005/0187793 A1 | 8/2005 | Myles | |
| 2005/0197862 A1 | 9/2005 | Paterson et al. | |
| 2005/0240473 A1 | 10/2005 | Ayers, Jr. et al. | |
| 2005/0288972 A1 | 12/2005 | Marvin et al. | |
| 2006/0015518 A1 | 1/2006 | Eletreby et al. | |
| 2006/0020514 A1 | 1/2006 | Yered | |
| 2006/0026041 A1 | 2/2006 | Ullman | |
| 2006/0085230 A1 | 4/2006 | Brill et al. | |
| 2006/0149587 A1* | 7/2006 | Hill et al. | 705/2 |
| 2006/0149784 A1 | 7/2006 | Tholl et al. | |
| 2006/0184391 A1 | 8/2006 | Barre et al. | |
| 2006/0224415 A1 | 10/2006 | Hudson et al. | |
| 2006/0229915 A1 | 10/2006 | Kosinski et al. | |
| 2006/0247948 A1 | 11/2006 | Ellis et al. | |
| 2006/0259363 A1 | 11/2006 | Jhetam et al. | |
| 2006/0265245 A1 | 11/2006 | McCallie et al. | |
| 2006/0271398 A1 | 11/2006 | Belcastro | |
| 2006/0271402 A1 | 11/2006 | Rowe et al. | |
| 2006/0271405 A1 | 11/2006 | Cipolle et al. | |
| 2006/0287886 A1 | 12/2006 | Kitazawa | |
| 2007/0005402 A1 | 1/2007 | Kennedy et al. | |
| 2007/0050209 A1 | 3/2007 | Yered | |
| 2007/0088576 A1 | 4/2007 | de Beus et al. | |
| 2007/0124177 A1 | 5/2007 | Engleson et al. | |
| 2007/0136100 A1 | 6/2007 | Daugherty et al. | |
| 2007/0162303 A1 | 7/2007 | Wiley et al. | |
| 2007/0179957 A1 | 8/2007 | Gibson et al. | |
| 2007/0233525 A1 | 10/2007 | Boyle | |
| 2007/0233526 A1 | 10/2007 | Hoffman et al. | |
| 2007/0239493 A1* | 10/2007 | Sweetland et al. | 705/4 |
| 2008/0126117 A1 | 5/2008 | Miller et al. | |
| 2008/0313103 A1 | 12/2008 | Burns et al. | |
| 2009/0048864 A1 | 2/2009 | Kozlowski et al. | |
| 2009/0222289 A1 | 9/2009 | Helmus et al. | |
| 2009/0313039 A1* | 12/2009 | Cedergreen | 705/2 |
| 2010/0180223 A1 | 7/2010 | Speier | |
| 2010/0324936 A1 | 12/2010 | Vishnubhatla et al. | |

FOREIGN PATENT DOCUMENTS

| | | |
|---|---|---|
| WO | WO 9106917 A1 | 5/1991 |
| WO | WO 9503569 A3 | 2/1995 |
| WO | WO 9725682 A1 | 7/1997 |
| WO | WO 9850871 A1 | 11/1998 |
| WO | WO 0039737 A1 | 7/2000 |
| WO | WO 2007025295 A2 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-32. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005.

Non-Final Office Action for U.S. Appl. No. 11/441,554 mailed Nov. 24, 2009.

Non-Final Office Action for U.S. Appl. No. 11/608,068 mailed Jan. 11, 2010.

Final Office Action for U.S. Appl. No. 11/608,068 mailed May 10, 2010.

Final Office Action for U.S. Appl. No. 11/441,554 mailed May 11, 2010.

Non-Final Office Action for U.S. Appl. No. 11/441,554 mailed Oct. 13, 2010.

Final Office Action for U.S. Appl. No. 11/441,554 mailed Mar. 17, 2011.

Non-Final Office Action for U.S. Appl. No. 12/713,945 mailed Dec. 20, 2011.

Non-Final Office Action for U.S. Appl. No. 12/696,717 mailed Jan. 6, 2012.

Non-Final Office Action for U.S. Appl. No. 12/714,003 mailed Jan. 20, 2012.

Wermes, Mark K. "Knowing claims switches can simplify your life." Drug Store News. p. 70. Nov. 23, 1992.

Final Office Action for U.S. Appl. No. 11/608,068 mailed Aug. 2, 2012.

Non-Final Office Action for U.S. Appl. No. 13/435,241 mailed Aug. 3, 2012.

Notice of Allowance for U.S. Appl. No. 11/441,554 mailed Aug. 21, 2012.

Non-Final Office Action for U.S. Appl. No. 13/435,245 mailed Jul. 19, 2012.

Non-Final Office Action for U.S. Appl. No. 11/608,068 mailed Apr. 12, 2012.

Final Office Action for U.S. Appl. No. 12/713,945 mailed May 2, 2012.

Final Office Action for U.S. Appl. No. 12/696,717 mailed May 30, 2012.

Final Office Action for U.S. Appl. No. 12/714,003 mailed Jun. 12, 2012.

Final Office Action for U.S. Appl. No. 12/714,003 mailed Sep. 12, 2012.

Final Office Action for U.S. Appl. No. 13/435,245 mailed Sep. 24, 2012.

Final Office Action for U.S. Appl. No. 13/435,241 mailed Dec. 6, 2012.

Point-of-Care Partners, "ePrescribing: Snapshot, Direction and Impact on Pharma" Bio/Phamaceutical Health Records and Data Summit; Oct. 22, 2007.

Cote, Bryan; "Adoption of e-prescribing yields surprising benefits to practices," Oncology business review, May 2009.

(56) References Cited

OTHER PUBLICATIONS

McKesson, "eScript" Mar. 2009.
Non-Final Office Action for U.S. Appl. No. 12/980,999 mailed Mar. 7, 2013.
Non-Final Office Action for U.S. Appl. No. 11/608,068 mailed Jun. 17, 2013.
Final Office Action for U.S. Appl. No. 12/980,999 mailed Jun. 18, 2013.

* cited by examiner

SYSTEMS AND METHODS FOR SHIFTING PRESCRIPTION MARKET SHARE BY PRESENTING PRICING DIFFERENTIALS FOR THERAPEUTIC ALTERNATIVES

CROSS-REFERENCE TO RELATED APPLICATIONS

The present application is a divisional of and claims the benefit of U.S. patent application Ser. No. 11/608,068, entitled "Systems and Methods for Shifting Prescription Market Share by Presenting Pricing Differentials for Therapeutic Alternatives," filed Dec. 7, 2006, which claims the benefit of U.S. Provisional Application No. 60/748,432, filed Dec. 8, 2005, which are both incorporated by reference in their entirety.

FIELD OF THE INVENTION

Aspects of the invention relate generally to prescriptions, and more particularly, to systems and methods for driving market share for medications or pharmaceutical manufacturers or providers by presenting pricing differentials for therapeutic alternatives.

BACKGROUND OF THE INVENTION

The cost for prescription drugs and other medicines can be a recurring and increasing expense for many consumers. Pharmaceutical companies and generic drug manufacturers or providers can offer consumers competing drug and medicine products at different, sometimes substantially different, prices. In many instances, consumers may be unaware of the availability of and relative prices between the variety of drug and medicine product choices, including alternative drugs such as generic drugs.

In many instances, a consumer may be prescribed a brand name drug by his or her physician, which may be relatively more expensive than other competing, alternative drugs, such as a generic drug with therapeutically equivalent effects. Sometimes, a consumer can obtain information regarding alternative drug products by asking his or her physician and/or pharmacist whether such alternative or generic drugs exist. In other instances, a consumer can determine similar information by conducting independent research.

Obtaining alternative drug product information from a physician and/or pharmacist or by conducting independent research can be difficult and time consuming. A common drawback to asking a physician whether alternative drug products exist is that the physician may not know the relative costs of the alternative drug products compared to a prescribed drug. A drawback to asking a physician and/or pharmacist whether alternative drug products exist is that the consumer must be sophisticated enough to ask his or her physician and/or pharmacist whether alternative drug products exist. A drawback to conducting independent research for such drug products is that the research may be relatively technical, and there is a possibility that a consumer could misidentify a drug product, or misidentify a dosage of a particular alternative drug that is not a relatively safe alternative to the initially prescribed drug.

Therefore, a need exists for systems and methods for identifying an alternative to prescription drug products.

In addition, a need exists for systems and methods for obtaining an alternative to a prescription drug from a pharmacy.

Furthermore, a need exists for systems and methods for facilitating a shift in drug market share.

Moreover, a need exists for systems and methods for enhancing revenues of a pharmacy.

An additional need exists for systems and methods for driving market share for medications or pharmaceutical manufacturers or providers by presenting pricing differentials for therapeutic alternatives.

SUMMARY OF THE INVENTION

Embodiments of the invention can provide some or all of the above needs. Embodiments of the invention can provide mechanisms for driving market share towards certain medications or pharmaceutical manufacturers or providers in the 100% co-pay (e.g., discount programs), cash, and funded (e.g., insurance plans) transaction marketplace. In an embodiment of the invention, the 100% co-pay and cash transactions described with respect to systems and methods disclosed herein, can be in accordance with transactions disclosed in U.S. Provisional Application No. 60/711,743, filed Aug. 26, 2005, and entitled "SYSTEMS AND METHODS FOR PROVIDING PHARMACY DISCOUNTS FOR CASH CUSTOMERS WHILE MAINTAINING THIRD-PARTY REIMBURSEMENT RATES," the contents of which are hereby incorporated by reference. In particular, as described by embodiments in further detail below, the 100% co-pay and cash transactions may be facilitated between a pharmacy and a switch provider, which may implement mechanisms for driving market share towards certain medications or pharmaceutical manufacturers In accordance with embodiments of the invention, a consumer may be provided with certain information in order to provide incentives to the consumer to select another medication or pharmaceutical manufacturer or provider. In particular, the consumer ordering a particular medication may be presented with information regarding other medications that may meet the consumer's health requirements by providing the same therapeutic results. If there are other medications that will meet the consumer's health requirements, then the consumer may also be presented with information specifying which, and the extent to which, those other medications will decrease the consumer's medication costs.

In accordance with another embodiment of the invention, a Therapeutic Alternative Program may be implemented that provides mechanisms for driving current 100% co-pay and cash consumer purchase decisions toward a preferred manufacturer's or provider's products, thereby creating a market shift for the preferred manufacturer or provider. In this example embodiment, a consumer may present a prescription for a medication to a pharmacy. The pharmacy receiving such a request may transmit an electronic claim, via modem, lease line or other electronic data transmission medium over a network, to a switch provider such as NDCHealth's Intelligent Network. The switch provider may interconnect one or more pharmacies with one or more pharmacy benefit managers (PBMs) using one or more networks, including private networks or the Internet. The electronic claim from the pharmacy may identify the medication, and in some embodiments, the pharmacy's current pricing information.

Next, the switch provider may compare the submitted medication with a set of pharmaceutical products known to have the same or similar therapeutic effects. With respect to the set of pharmaceutical products, the switch provider has already contracted with pharmaceutical manufacturers or providers to obtain market share related volume rebates. From the set of pharmaceutical products known to have the same or similar therapeutic effects, the switch provider will then determine equivalent dosages of the alternative products. Having determined the equivalent dosages of the alternative products, the switch provider can then determine whether those particular alternative products will result in a cost savings to the consumer compared to the originally requested medication.

In accordance with an embodiment of the invention, the switch provider may access or otherwise include a data storage device, database, or other look-up table for determining equivalent dosages of the alternative products as well as the potential cost savings. In particular, the switch provider may maintain a database or table of non-preferred pharmaceutical products as well as a database or table of preferred pharmaceutical products that have equivalent therapeutic effects as the non-preferred pharmaceutical products. Using the database and/or tables, each of these non-preferred pharmaceutical products may be cross-referenced with preferred pharmaceutical products known to have equivalent therapeutic effects. In addition, the database and/or tables will also have specified equivalent dosages between the preferred and non-preferred drugs. Further, pricing information for the preferred pharmaceutical products will be included. In accordance with one embodiment of the invention, this pricing information may be set by the pharmacy. In another embodiment of the invention, the pricing information may be set by the switch provider, perhaps based in part upon previously-negotiated rebates with manufacturers or providers. Other embodiments may have pricing information set by the pharmacy benefits managers (PBMs).

Accordingly, if the switch provider is able to identify one or more alternative medications that result in a cost savings to the consumer, the switch provider may not complete the initial request for the original medication. Instead, the switch provider may transmit a message to the pharmacy, for example, stating perhaps "Preferred Drug Entity A will save you $xx.xx. To override this rejection, enter XXXX into the prior authorization field." As described above, the preferred drug entity A may be one of the items for which the switch provider has a contract in place with the manufacturer or provider of drug entity A to provide volume rebates in exchange for positive market share shift. A portion of the rebate dollars that are generated by this contract may be provided to the pharmacy in order to incentivize them to participate in this Therapeutic Alternative Program and to provide a greater cash pricing differential for the preferred medications as compared to the non-preferred medications.

In accordance with another example embodiment of the invention, the Therapeutic Alternative Program's functionality may also be implemented in the funded transaction market by providing similar messaging to the pharmacy informing them of therapeutically-equivalent medications on the payer's preferred drug list and a lower co-pay cost associated with the use of those items as compared to the ones that are absent from that list. One of ordinary skill in the art will readily recognize that many other variations of the Therapeutic Alternative Program are possible.

Therefore various systems and processes according to embodiments of the invention can include:

(1) Systems and methods for identifying an alternative to prescription drug products;

(2) Systems and methods for obtaining an alternative to a prescription drug from a pharmacy;

(3) Systems and methods for facilitating a shift in drug market share;

(4) Systems and methods for enhancing revenues of a pharmacy; and (5) Systems and methods for driving market share for medications or pharmaceutical manufacturers or providers by presenting pricing differentials for therapeutic alternatives.

Other systems and processes according to various embodiments of the invention will become apparent with respect to the remainder of this document.

BRIEF DESCRIPTION OF THE DRAWINGS

Reference will now be made to the accompanying drawings, which are not necessarily drawn to scale, and wherein.

DETAILED DESCRIPTION

Figure 1:
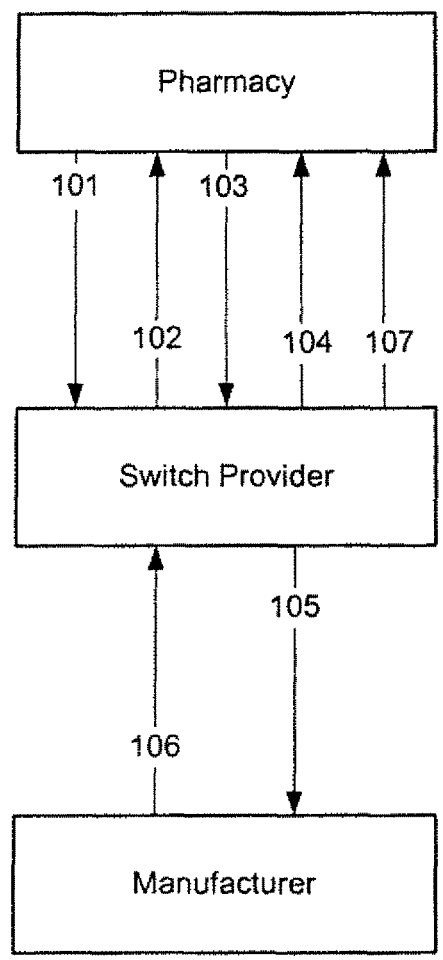
FIG. 1 illustrates an example embodiment of the invention where a 100% co-pay plan is hosted by a switch provider.

The invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The invention is described below with reference to block diagrams and flowchart illustrations of systems, methods, apparatuses and computer program products according to embodiments of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational elements or steps to be performed on the computer or other programmable apparatus to produce a computer implemented process such that the instructions that execute on the computer or other programmable apparatus provide elements or steps for implementing the functions specified in the flowchart block or blocks.

Accordingly, blocks of the block diagrams and flowchart illustrations support combinations of means for performing the specified functions, combinations of elements or steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perforin the specified functions, elements or steps, or combinations of special purpose hardware and computer instructions.

The terms "alternative drug", "therapeutic alternative", "therapeutic equivalent", "therapeutic equivalent drug", "therapeutically equivalent drug", and "therapeutically equivalent item" are used interchangeably throughout the description, and should be construed to cover any drug, medication, or chemical composition having the same effects, similar effects, or substantially similar therapeutic effects on a person, patient, or consumer as a prescribed drug, medication, or chemical composition when taken in an appropriate dosage.

Figure 2:
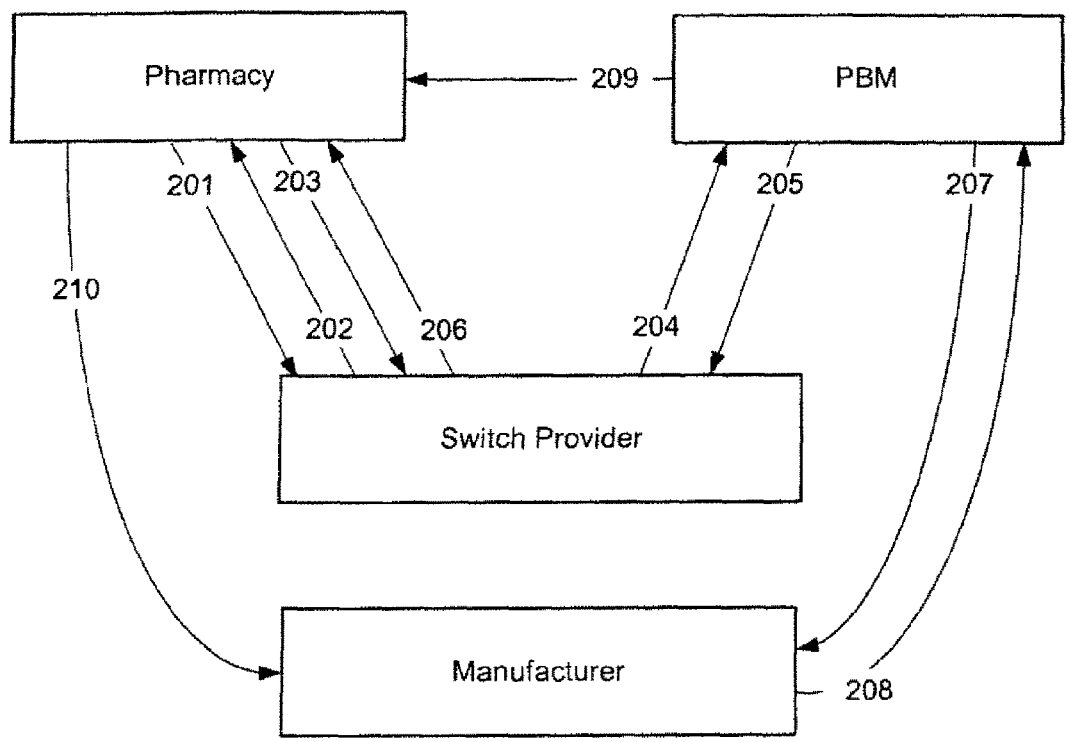
FIG. 2 illustrates an example embodiment of the invention where a 100% co-pay plan is hosted by an entity other than a switch provider.
Figure 3:
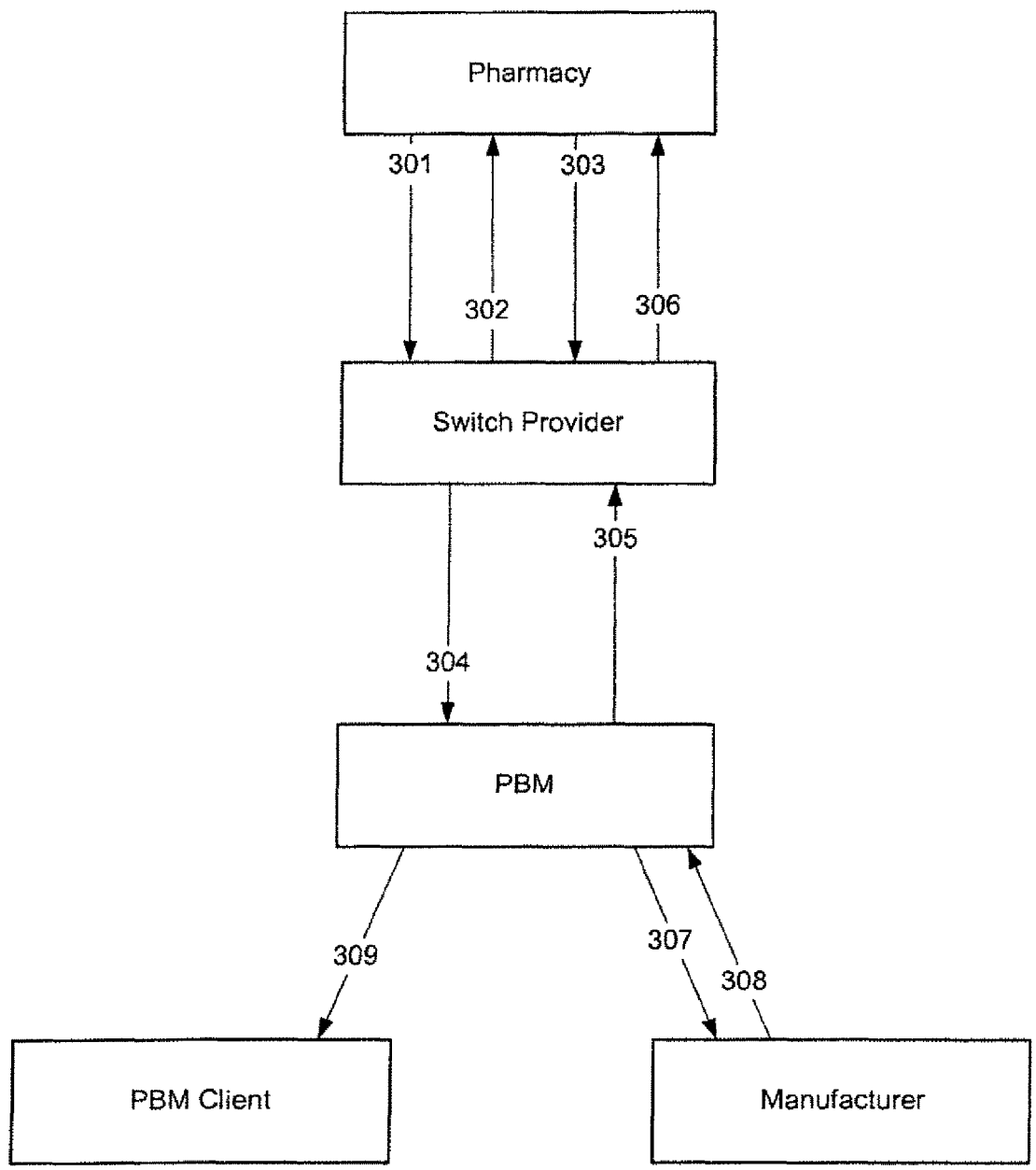
FIG. 3 illustrates an example embodiment of the invention involving funded plans.

Having generally described the operation of the Therapeutic Alternative Program, three example embodiments of the Therapeutic Alternative Program will now be described with reference to FIGS. 1-3.

Example 1

100% Co-Pay Plan Hosted by Switch Provider

In a first embodiment of the invention, a switch provider may host a Therapeutic Alternative Program (TAP) or therapeutic alternative program module in addition to a 100% co-pay plan. In this first embodiment of the invention, a transaction received at the switch provider from the pharmacy may be exposed to a system of editing functionality that will compare the submitted drug entity and dosage to a known set of therapeutically-equivalent preferred items. Based upon the submitted drug entity and dosage submitted, the switch provider may populate a list of equivalent drug entities, dosages, and the respective pricing, available manufacturer or provider rebates, coupons, vouchers, patient assistance, or similar price reduction methodologies associated with each. If a therapeutically-equivalent entity exists on this list, that item(s) will be utilized to populate the messaging notifying the pharmacy of the preferred entity. The pricing will be utilized to calculate the difference between the non-preferred item (e.g., the originally submitted drug entity) and the preferred entity and will also populate the messaging. The transaction may then be returned to the pharmacy as a rejected claim. If the pharmacy chooses to override the rejection, they will enter the appropriate (provided) override code into the prior authorization field and the claim will be allowed to transact without further intervention. The next time that claim is submitted, the pharmacy may receive the same message and may have to choose what action to take. If the pharmacy educates the patient and the physician about the opportunity and a change is made to the preferred item, the pharmacy will submit a claim for a preferred item instead. On the other hand, the editing system may not invoke a rejection when the claim is submitted for a preferred item. One of ordinary skill in the art will recognize that current cash transactions would essentially become 100% co-pay transactions that are processed as indicated above.

This first embodiment will now be described with reference to FIG. 1. In FIG. 1, as shown in 101, a transaction leaves the pharmacy and enters the switch provider's TAP before it reaches the switch provider's 100% co-pay plan where pricing of the claim would be set. In 101, the switch provider will determine the therapeutic alternatives and calculate the cost savings by utilizing the therapeutic alternative price compared to the submitted price. The true price for the both items will be calculated by utilizing the 100% co-pay plan's rules for discounts. The true prices will be compared and the messaging will be created and sent back to the pharmacy in 102. In particular, in 102, the messaging of a therapeutically equivalent drug, dosage and cost savings will be communicated to the pharmacy. The pharmacy may print (or otherwise communicate) the messaging to provide to the patient. If the patient requests to try the alternative drug, the pharmacy will call the physician for approval. The pharmacy will provide the physician with the therapeutically-equivalent drug name, dosage, and cost savings for the patient. If the physician chooses to make the change, the pharmacy will re-submit the prescription claim for the alternate drug. If the change is not approved by either the patient or the physician, the pharmacy can override the rejection and re-submit the original drug.

Next, in 103, the pharmacy will submit either the original drug or the preferred alternative. If it is the original drug, the Therapeutic Alternative Program or therapeutic alternative program module may check to make sure the pharmacy entered the proper override code. Once verified, the transaction may proceed to the 100% co-pay plan hosted at the switch provider for pricing based on the rules within that program. If it is the alternative drug, the transaction will proceed to the 100% co-pay plan hosted at the switch provider for pricing based on the rules within that program. In 104, the switch provider may return, to the pharmacy, the correct pricing for the drug entity requested based on the rules contained in the 100% co-pay plan hosted at the switch provider.

Now referring to 105, the switch provider may capture all of the data elements necessary from its pharmacy participants and compile it into a format that will provide information concerning market share shifts attained for the specific drug entities for which pharmaceutical manufacturers or providers have contracted to provide volume rebates for such shifts. The switch provider will then provide this information to the pharmaceutical manufacturers or providers to obtain the rebate revenues on behalf of its pharmacy participants. As shown in 106, the pharmaceutical manufacturer or provider may provide rebate revenues to the switch provider as provided for in the contractual agreements between the two parties. In 107, the switch provider will sort the rebate revenues based on market share shift attained by the different pharmacy participants and provide a portion of these revenues to the pharmacy participants, withholding a previously agreed upon amount for the act of providing this functionality, aggregation, revenue attainment and disbursement.

Example 2

100% Co-Pay Plan Hosted by an Entity Other than the Switch Provider

In a second embodiment of the invention, the switch provider may host a Therapeutic Alternative Program (TAP), but the 100% co-pay plan may be hosted by an entity other than the switch provider. Accordingly, in this second embodiment, the claim will come to the switch provider while on its way to a 100% co-pay claims processor, such a Pharmacy Benefits Manage (PBM). The Therapeutic Alternative Program will function in substantially the same way as described above, except the market share shift may be driven by the preferred drug list that is in place at the switch provider instead of any preferred drug list that may or may not be in place at the 100% co-pay claims processor.

This second embodiment will now be described with reference to FIG. 2. In FIG. 2, as shown in 201, a transaction leaves the pharmacy and enters the switch provider's TAP before it reaches the hosted 100% co-pay plan at the PBM where pricing of the claim would be set. In 201, the therapeutic alternatives will be determined and the cost savings will be calculated by utilizing the therapeutic alternative price compared to the submitted price. The true price for the both items will be calculated by utilizing the 100% co-pay plan's rules for discounts. The true prices will be compared and the messaging will be created and sent back to the pharmacy (202). In 202, a messaging containing a therapeutically equivalent drug, dosage and cost savings will be communicated to the pharmacy. The pharmacy may print the messaging (or otherwise communicate) to provide to the patient. If the patient requests to try the alternative drug, the pharmacy will call the physician for approval. The pharmacy will provide the physician with the therapeutically-equivalent drug name, dosage, and cost savings for the patient. If the physician chooses to make the change, the pharmacy will re-submit the prescription claim for the alternate drug. If the change is not approved by either the patient or the physician, the pharmacy can override the rejection and re-submit the original drug.

As shown in 203, the pharmacy may submit either the original drug or the preferred alternative. If it is the original drug, the Therapeutic Alternative Program will check to make sure the pharmacy entered the proper override code. In 204, the switch provider will forward the claim to the Prescription Benefits Manager (PBM) that hosts the 100% co-pay plan for appropriate pricing. In 205, the PBM will return the claim to the switch provider in order for it to be returned to the pharmacy. The switch provider will return the claim to the pharmacy as shown in 206.

In 207, the PBM will aggregate all of the claims from its pharmacy participants and submit the appropriate information to manufacturers or providers for any rebate dollars that are available for 100% co-pay claims that have not been exposed to market-share influencing functionality (the Therapeutic Alternative Program functionality). In 208, the PBM may receive some amount of volume rebates from manufacturers or providers. In 209, the PBM may provide some share of these rebates to the pharmacy participant(s). As shown in 210, the pharmacy has its own separate contracts with the manufacturers or providers to provide functionality that will provide market share shift toward that specific manufacturer's or provider's product(s) (the Therapeutic Alternative Program). The pharmacy submits the appropriate data to the pharmaceutical manufacturer or provider in order to obtain volume rebate revenue for the market share shift that was attained.

Example 3

Funded Plans

A third embodiment of the invention may involve the use of a switch provider's Therapeutic Alternative Program (TAP) in the funded transaction marketplace. In this third embodiment, the preferred drug list would be provided by the funded program (Prescription Benefits Manager or PBM) along with the means of identifying the patient and the co-pay differentials associated with the consumer choosing a preferred item. The claim would come to the switch provider where it would be subjected to editing to determine the presence of one or more alternative, preferred item(s) and the co-pay differential associated with using one of the preferred item(s). That information would be returned to the pharmacy in the same fashion as previously described.

This third embodiment will now be described with reference to FIG. 3. In FIG. 3, as shown in 301, a transaction leaves the pharmacy and enters the switch provider's TAP before it reaches the PBM for adjudication. In the TAP, the submitted drug entity will be compared to the list of preferred drugs within the same therapeutic category as provided by the PBM. If it is not on that list, the co-pay differential will be obtained from information provided by the PBM and the transaction will be rejected to the pharmacy. In 302, in the rejected transaction a message will be inserted that will identify the preferred therapeutic alternatives and the co-pay savings that with patient will realize if one of the preferred alternatives are chosen. The pharmacy may choose either to override the rejection and fill for the original drug or he may educate the patient and the physician as necessary to cause a change to the preferred drug entity.

Next, in 303, the pharmacy may submit either the original drug or the interchanged, preferred drug entity. The transaction will enter the TAP program and be examined for either an appropriate override code or a preferred drug entity. Once this has been verified, the claim is passed on to the PBM for adjudication and pricing (304). In 305, the claim is returned to the switch provider in order to be returned to the pharmacy. The claim is returned to the pharmacy as shown in 306.

As shown in 307, the PBM aggregates all of the claims that were submitted for its managed participants and submits the appropriate information to pharmaceutical manufacturers or providers in order to obtain volume rebates according to the contracts it has in place for the services provided. The pharmaceutical manufacturer or provider may provide to the PBM volume rebate dollars according to their contractual agreements as shown in 308. In 309, the PBM may or may not share these rebate dollars with its clients, typically an employer.

As described above, the cost savings based on a therapeutically-equivalent item may be determined on a known quantity basis. Alternatively, the cost savings may be determined on a per drug per day basis. One of ordinary skill in the art will readily recognize that many alternatives exist as a basis for determining the cost savings.

Figure 4:
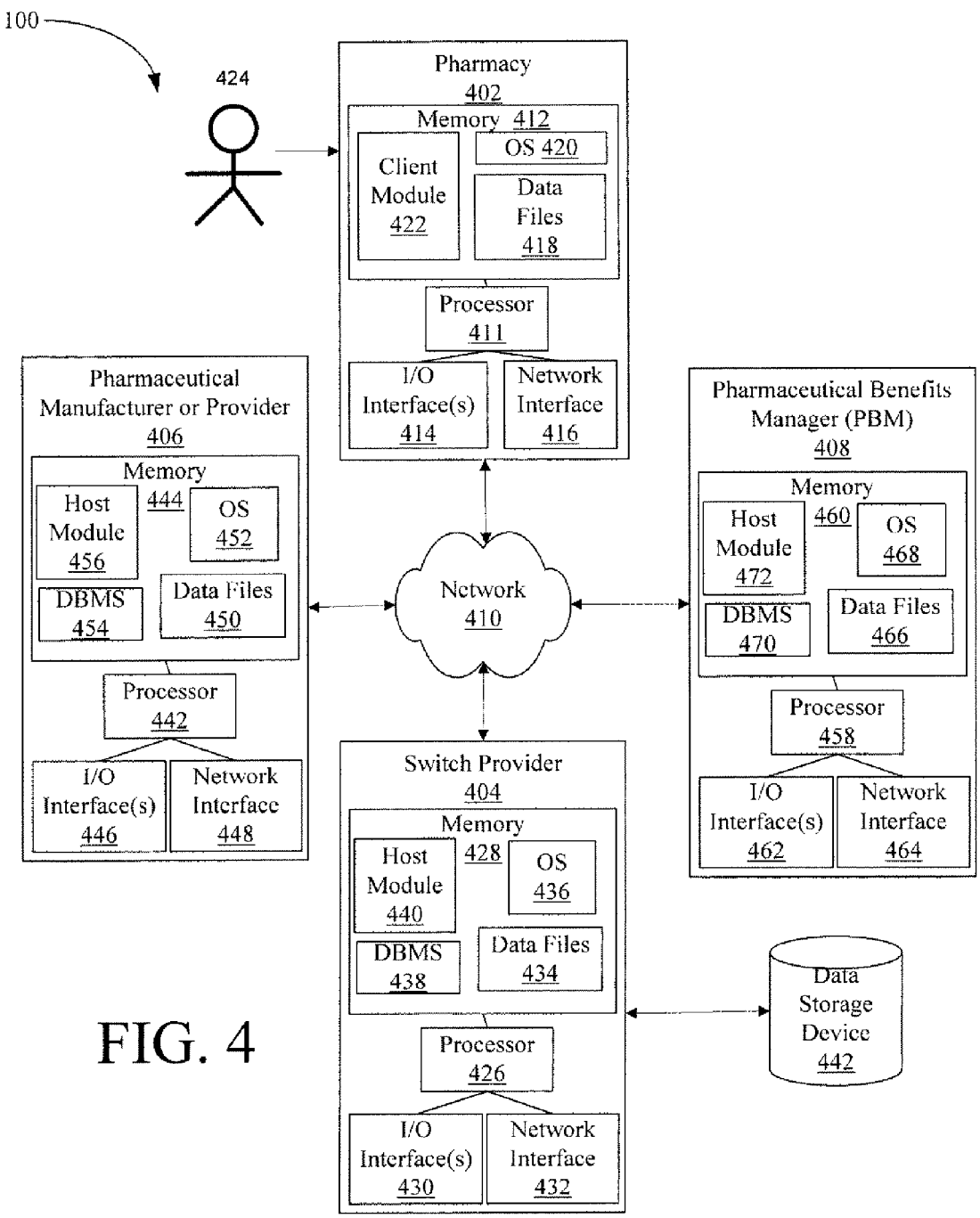
FIG. 4 illustrates an example system in accordance with an embodiment of the invention.

An example system in accordance with an embodiment of the invention is shown in FIG. 4. FIG. 4 shows a block diagram of a therapeutic alternative program system 100 for facilitating driving a drug market share, according to embodiments of the invention. In particular, the therapeutic alternative program system 400 of FIG. 4 includes at least one pharmacy 402, at least one switch provider 404, and at least one pharmaceutical manufacturer or provider 406, which are each configured for accessing and reading associated computer-readable media having stored thereon data and/or computer-executable instructions for implementing the various methods of the invention. In another embodiment of the invention, a therapeutic alternative program system 400 of FIG. 4 can include at least one pharmaceutical benefits manager (PBM) 408, which may be configured for accessing and reading associated computer-readable media having stored thereon data and/or computer-executable instructions for implementing the various methods of the invention. Generally, network devices and systems, including the one or more pharmacies 402, switch providers 404, pharmaceutical manufacturers or providers 406, and pharmaceutical benefits managers (PBM) 408 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 4, a pharmacy 402, switch provider 404, pharmaceutical manufacturer or provider 406, and PBM 408 may be in direct communication with each other or via a network 410, which as described below can include one or more private and public networks, including the Internet. In other embodiments, multiple pharmacies, switch providers, pharmaceutical manufacturers or providers, and PBMs may exist. Each of these components the pharmacy 402, the switch provider 404, switch provider 404, pharmaceutical manufacturer or provider 406, PBM 408, and the network 410—will now be discussed in turn. First, the pharmacy 402 may be any processor-driven device, such as a personal computer, laptop computer, handheld computer, and the like. In addition to having a processor 411, the pharmacy 402 may further include a memory 412, input/output ("I/O") interface(s) 414 and a network interface 416. The memory 412 may store data files 418 and various program modules, such as an operating system ("OS") 420 and a client module 422. The client module 422 may be an Internet browser or other software, including a dedicated program, for interacting with the switch provider 404. For example, a user 424, such as a consumer, pharmacist, or other pharmacy employee, may utilize the client module 422 in preparing and providing a prescription drug request or order to the switch provider 404 for processing. The pharmacy 402 may also utilize the client module 422 to retrieve or otherwise receive data from the switch provider 404, including pricing and discount information for the prescription drug request or order, and pricing and discount information for any alternative drugs.

Still referring to the pharmacy 402, the I/O interface(s) 414 facilitate communication between the processor 411 and various I/O devices, such as a keyboard, mouse, printer, microphone, speaker, monitor, bar code readers/scanners, RFID readers, and the like. The network interface 416 may take any of a number of forms, such as a network interface card, a modem, a wireless network card, and the like. These and other components of the pharmacy 402 will be apparent to those of ordinary skill in the art and are therefore not discussed in more detail herein.

Similar to the pharmacy 402, the switch provider 404 may include any processor-driven device that is configured for receiving, processing, and fulfilling requests from the pharmacy 402 related to pharmacy, benefits, and/or discount transactions, including those associated with therapeutic alternative program system. The switch provider 404 may therefore include a processor 426, a memory 428, input/output ("I/O") interface(s) 430, and a network interface 432. The memory 428 may store data files 434 and various program modules, such as an operating system ("OS") 436, a database management system ("DBMS") 438, and the host module 440. The host module 440 receives, processes, and responds to requests from the respective client module 422 of pharmacy 402, and further receives, processes, and responds to requests from the respective host modules 456, 472 of the pharmacy manufacturer or provider 406 and PBM 408. The switch provider 404 may include additional program modules for performing other pre-processing or post-processing methods described herein. Those of ordinary skill in the art will appreciate that the switch provider 404 may include alternate and/or additional components, hardware or software.

As illustrated in FIG. 1, the switch provider 404 may include or be in communication with at least one data storage device 442, or databases. If the switch provider 404 includes the data storage device 442, then the data storage device 442 could also be part of the memory 428. The data storage device 442 and/or memory 428 may store, for example, program rules and transaction records, rebates, and/or discounts associated with prescription drug requests and orders. The data storage device 442 and/or memory 428 may also store alternative drug information (e.g., equivalent drug names, equivalent dosage amounts, cost and pricing information, etc.) for comparing prescription drug requests and orders. Although a single data storage device 442 is referred to herein for simplicity, those skilled in the art will appreciate that multiple physical and/or logical data storage devices or databases may be used to store the above mentioned data. For security and performance purposes, the switch provider 404 may have a dedicated connection to the data storage device 442. However, the switch provider 404 may also communicate with the data storage device 442 via a network 410, as shown. In other embodiments of the invention, the switch provider 404 may include the data storage device 442 locally. The switch provider 404 may also otherwise be part of a distributed or redundant DBMS.

Similar to the pharmacy 402 and the switch provider 404, the pharmaceutical manufacturer or provider 406 may include any processor-driven device that is configured for receiving, processing, and fulfilling requests from the pharmacy 402 and/or switch provider related to pharmacy, benefits, and/or discount transactions, including those associated with the therapeutic alternative program system. The pharmaceutical manufacturer or provider 406 may therefore include a processor 442, a memory 444, input/output ("I/O") interface(s) 446, and a network interface 448. The memory 444 may store data files 450 and various program modules, such as an operating system ("OS") 452, a database management system ("DBMS") 454, and the host module 456. The host module 456 receives, processes, and responds to requests from the client module 422 of pharmacy 402, and further receives, processes, and responds to requests from the respective host modules 440, 472 of the switch provider 404 and PBM 408. The pharmaceutical manufacturer or provider 406 may include additional program modules for performing other pre-processing or post-processing methods described herein. Those of ordinary skill in the art will appreciate that the pharmaceutical manufacturer or provider 406 may include alternate and/or additional components, hardware or software.

Similar to the switch provider 404, the pharmaceutical manufacturer or provider 406 may include or be in communication with at least one data storage device or database, similar to 442.

Similar to the pharmacy 402, switch provider 404, and pharmaceutical manufacturer or provider 406, the PBM 408 may include any processor-driven device that is configured for receiving, processing, and fulfilling requests from the pharmacy 402, switch provider 404 and/or pharmaceutical manufacturer or provider 406 related to pharmacy, benefits, and/or discount transactions, including those associated with the therapeutic alternative program system. The PBM 408 may therefore include a processor 458, a memory 460, input/output ("I/O") interface(s) 462, and a network interface 464. The memory 460 may store data files 466 and various program modules, such as an operating system ("OS") 468, a database management system ("DBMS") 470, and the host module 472. The host module 472 receives, processes, and responds to requests from the client module 422 of pharmacy 402, and further receives, processes, and responds to requests from the respective host modules 440, 456 of the switch provider 404 and pharmaceutical manufacturer or provider 406. The PBM 408 may include additional program modules for performing other pre-processing or post-processing methods described herein. Those of ordinary skill in the art will appreciate that the PBM 408 may include alternate and/or additional components, hardware or software.

Similar to the switch provider 404, and pharmaceutical manufacturer or provider 406, the PBM 408 may include or be in communication with at least one data storage device or database, similar to 442.

The network 410 may include any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 410 may also allow for real-time, off-line, and/or batch transactions to be transmitted between the pharmacy 402 and the switch provider 404. Due to network connectivity, various methodologies as described herein may be practiced in the context of distributed computing environments. Although the pharmacy 402 is shown for simplicity as being in communication with the switch provider 404 via one intervening network 410, it is to be understood that any other network configuration is possible. For example, intervening network 410 may include a plurality of networks, each with devices such as gateways and routers for providing connectivity between or among networks 410. Instead of or in addition to a network 410, dedicated communication links may be used to connect the various devices of the present invention.

Those of ordinary skill in the art will appreciate that the therapeutic alternative program system 400 shown in and described with respect to FIG. 4 is provided by way of example only. Numerous other operating environments, system architectures, and device configurations are possible. Accordingly, embodiments of the invention should not be construed as being limited to any particular operating environment, system architecture, or device configuration.

Embodiments of a therapeutic alternative program system, such as 400, can facilitate a shift in a drug market share of one or more pharmaceutical manufacturers or providers. Furthermore, embodiments of a therapeutic alternative program system, such as 400, can facilitate driving a drug market share of one or more pharmaceutical manufacturers or providers. The operation of a therapeutic alternative program system, such as 400 of FIG. 4, and its various components as well as associated methods and processes will now be described by reference to FIGS. 5-9.

Figure 5:
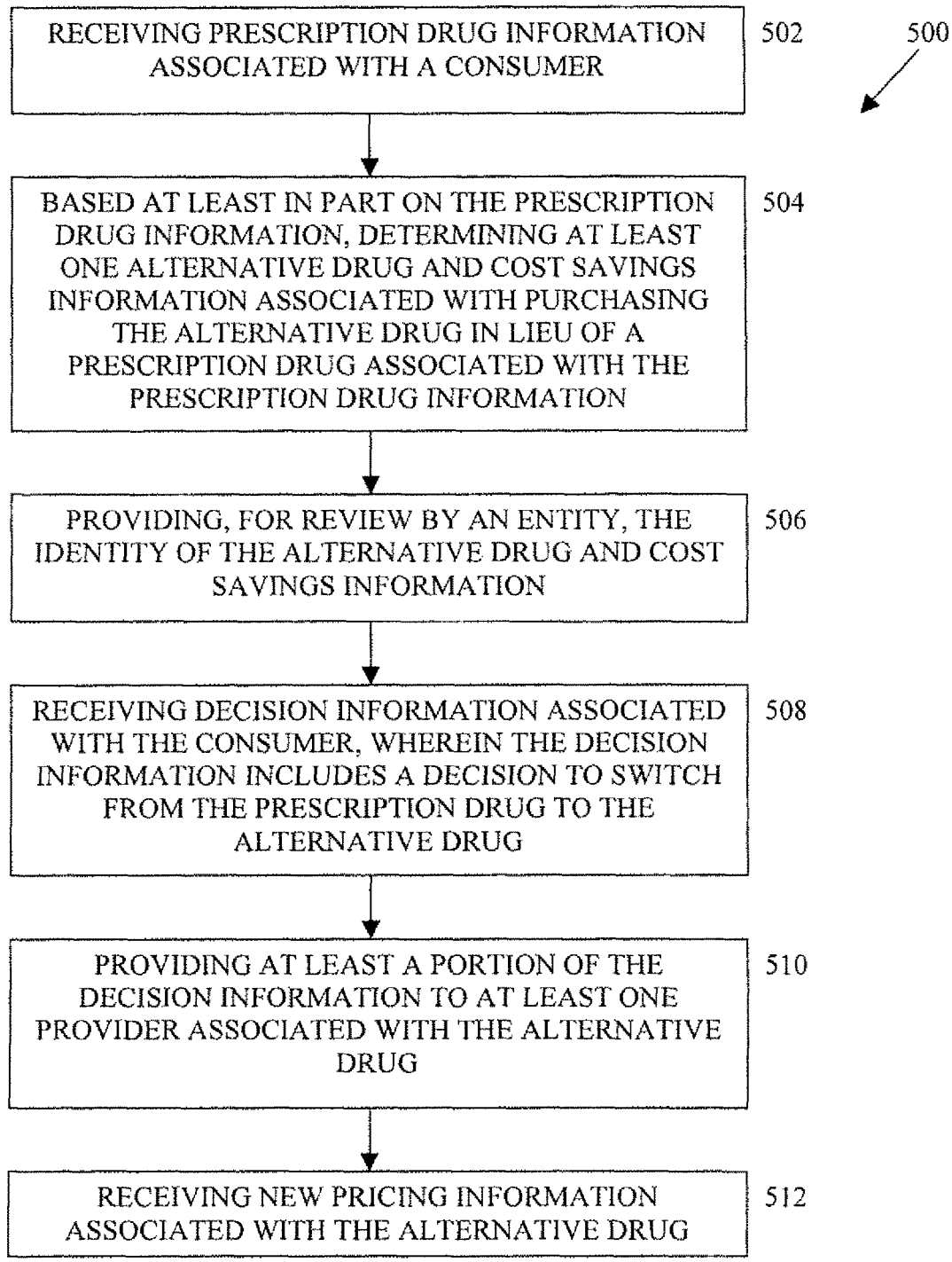
FIGS. 5-9 are process flowcharts illustrating example methods in accordance with embodiments of the invention.

FIGS. 5-9 are process flowcharts illustrating example methods in accordance with embodiments of the invention. The example method 500 shown in FIG. 5 provides a method for facilitating a shift in drug market share. The method 500 can be implemented by a therapeutic alternative program system, such as 400 of FIG. 4.

The method 500 begins at block 502. In block 502, prescription drug information associated with a consumer is received. For example, as shown in FIG. 4, prescription drug information associated with a consumer, such as 424, can be received by a pharmacy 402 via an I/O interface 414 and/or client module 422. The processor 411 associated with the pharmacy 402 can receive the prescription drug information and process and/or transmit the information as needed.

Block 502 is followed by block 504, in which based at least in part on the prescription drug information, at least one alternative drug and cost savings information associated with purchasing the alternative drug in lieu of a prescription drug associated with the prescription drug information are determined. For example, as shown in FIG. 4, a processor 411 can transmit the information via the network to a switch provider 404. The processor 426 associated with the switch provider 404 can determine one or more alternative drugs and calculate the cost savings by utilizing the difference in the alternative drug price and the price for a requested prescription drug. In one embodiment, the processor 426 can access a data storage device or database, such as 442, to obtain information associated with alternative drugs and the prescription drug.

In one embodiment, true prices for alternative drugs and a requested prescription drug can be calculated by using one or more discount rules. Examples of discount rules can include, but are not limited to, 100% co-pay plan rules for discounts, available manufacturer or provider rebates, coupons, vouchers, patient assistance, or similar price reduction methodologies associated with each. Based on the true prices, the processor 426 can calculate the cost savings.

Block 504 is followed by block 506, in which the identity of the alternative drug and cost savings information are provided for review by an entity. For example, as shown in FIG. 4, the processor 426 can transmit results via the network 410 to the pharmacy 402. The processor 411 associated with the pharmacy 402 can output the identity of the alternative drug and cost saving information via the I/O interface 414 and/or the client module 422. A consumer, such as 424, or other entity can review the identity of the alternative drug and cost savings information, including the name of a therapeutically equivalent drug, dosage, and cost savings, and the consumer 424 can make a decision regarding the selection of the alternative drug.

In one embodiment, an entity can be a pharmaceutical benefits manager, such as 408. For example, as shown in FIG. 4, the pharmacy 402 can transmit the identity of the alternative drug and cost savings information to the pharmaceutical benefits manager 408 for review. The processor 458 associated with the pharmaceutical benefits manager 408 can output the identity of the alternative drug and cost saving information via the I/O interface 462 and/or the host module 472. A person, such as 424, or other entity can review the identity of the alternative drug and cost savings information, and make a decision regarding the selection of the alternative drug.

Block 506 is followed by block 508, in which decision information associated with the consumer is received, wherein the decision information includes a decision to switch from the prescription drug to the alternative drug. For example, as shown in FIG. 4, a consumer, such as 424, can input decision information via the I/O interface 414 and/or the client module 422. The decision information, including a decision to switch from the prescription drug to the alternative drug, can be transmitted to the processor 411 for further processing.

In another embodiment, decision information can be input via the I/O interface 462 and/or the host module 472 associated with the pharmaceutical benefits manager 408. The decision information, including a decision to switch from the prescription drug to the alternative drug, can be transmitted to the processor 458 for further processing.

Block 508 is followed by block 510, in which at least a portion of the decision information is provided to at least one provider associated with the alternative drug. For example, as shown in FIG. 4, the processor 411 can transmit via the network 410 to a pharmaceutical manufacturer or provider 406 some or all of the decision information received from the consumer 424. In another embodiment, the processor 426 associated with the switch provider 404 can transmit via the network 410 to a pharmaceutical manufacturer or provider 406 some or all of the decision information received from the consumer 424. In some instances, the processor 411, 426 may capture all data elements necessary from various pharmacy participants and compile it into a format that will provide information concerning market share shifts attained for specific drug entities for which pharmaceutical manufacturers or providers 406 have contracted to provide volume rebates for such shifts.

Block 510 is followed by block 512, in which new pricing information associated with the alternative drug is received. For example, as shown in FIG. 4, the processor 442 associated with pharmaceutical manufacturer or provider 406 can receive some or all of the decision information associated with the consumer, and the processor 442 can determine whether the drug is eligible for a price reduction. If a particular drug is eligible for a rebate, the processor 442 can determine the appropriate rebate and transmit suitable pricing information via the network 410 to the pharmacy 402. In addition, the processor 442 can determine any rebate revenues for the pharmacy 402 or other pharmacy participants in accordance with any contractual agreements, such as between a pharmacy 402 and a pharmaceutical manufacturer or provider 406. The processor 442 can provide suitable rebate information via the network 410 to the switch provider 404, such that the switch provider 404 can determine or otherwise apportion any rebate revenues payable to the pharmacy 402 or other pharmacy participants.

The method 500 of FIG. 5 ends at block 510.

Figure 6:
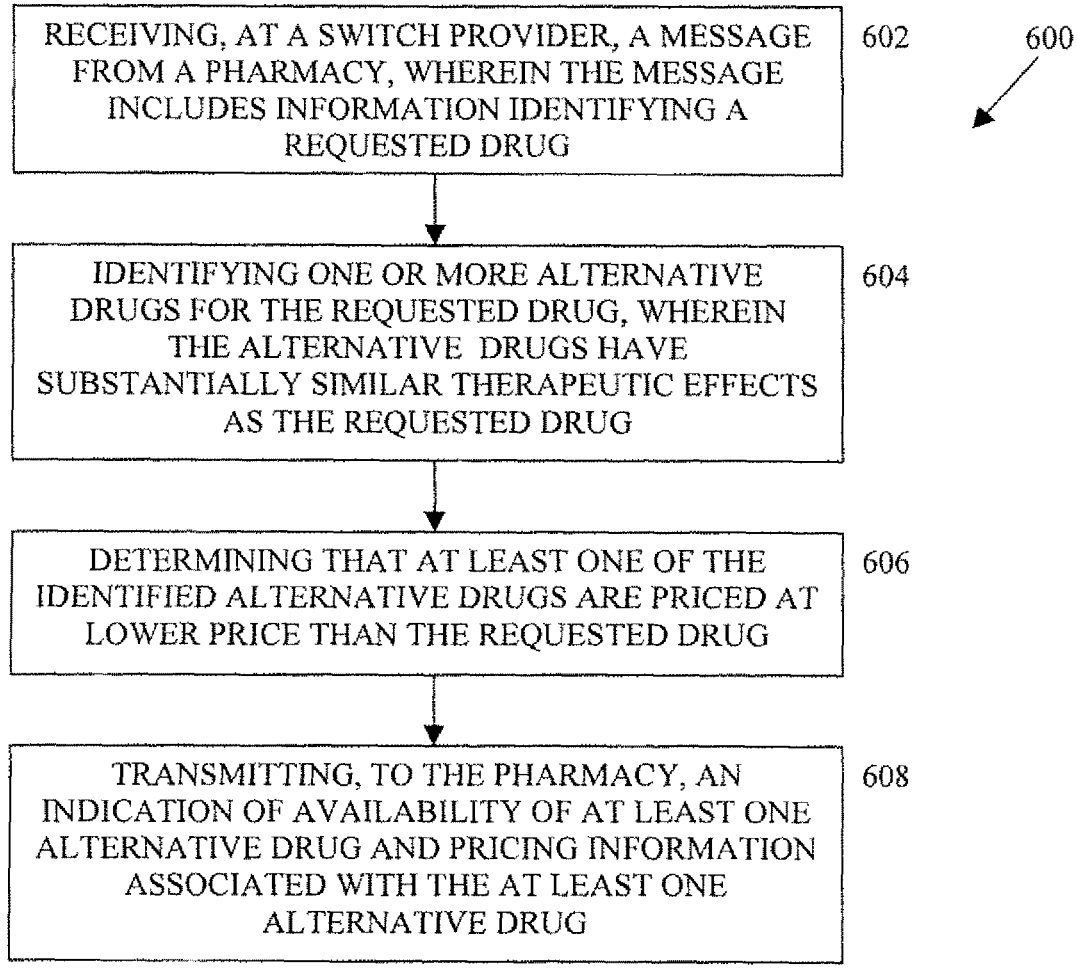

The example method 600 shown in FIG. 6 provides a method for facilitating a shift in drug market share. The method 600 can be implemented by a therapeutic alternative program system, such as 400 of FIG. 4.

The method 600 begins at block 602. In block 602, a message from a pharmacy is received, wherein the message includes information identifying a requested drug. For example, as shown in FIG. 4, prescription drug information associated with a consumer, such as 424, can be received by a pharmacy 402 via an I/O interface 414 and/or client module 422. The processor 411 associated with the pharmacy 402 can receive the prescription drug information and process and/or transmit the information as needed.

Block 602 is followed by block 604, in which one or more alternative drugs for the requested drug are identified, wherein the alternative drugs have substantially similar therapeutic effects as the requested drug. For example, as shown in FIG. 4, a processor 411 can transmit the information via the network to a switch provider 404. The processor 426 associated with the switch provider 404 can determine one or more alternative drugs, and compare the prices of an alternative drug and the price for the requested prescription drug. In one embodiment, the processor 426 can access a data storage device or database, such as 442, to obtain information associated with alternative drugs and the requested prescription drug.

In one embodiment, true prices for alternative drugs and a requested prescription drug can be calculated by using one or more discount rules. Examples of discount rules can include, but are not limited to, 100% co-pay plan rules for discounts, available manufacturer or provider rebates, coupons, vouchers, patient assistance, or similar price reduction methodologies associated with each. Based on the true prices, the processor 426 can calculate the cost savings.

Block 604 is followed by block 606, in which a determination is made that at least one of the identified alternative drugs is priced at a lower price than the requested drug. For example, as shown in FIG. 4, based on the processor 426 can determine that at least one identified alternative drug is priced relatively lower than the requested drug.

Block 606 is followed by block 608, in which an indication is transmitted of the availability of at least one alternative drug and pricing information associated with the at least one alternative drug. For example, as shown in FIG. 4, the processor 426 can transmit an indication via the network 410 to the pharmacy 402. The processor 426 can transmit the identity of the alternative drug, price, and in some instances, associated cost saving information, via the I/O interface 414 and/or the client module 422. A consumer, such as 424, or other entity can review the identity of the alternative drug and cost savings information, including the name of a therapeutically equivalent drug, dosage, and cost savings, and the consumer 424 can make a decision regarding the selection of the alternative drug.

In one embodiment, an entity can be a pharmaceutical benefits manager, such as 408. For example, as shown in FIG. 4, the processor 426 can transmit an indication via the network 410 to the pharmaceutical benefits manager 408 for review. The processor 458 associated with the pharmaceutical benefits manager 408 can output the identity of the alternative drug, price, and in some instances, cost saving information, via the I/O interface 462 and/or the host module 472. A person, such as 424, or other entity can review the identity of the alternative drug, price, and in some instances, cost savings information, and make a decision regarding the selection of the alternative drug.

The method 600 of FIG. 6 ends at block 608.

Figure 7:
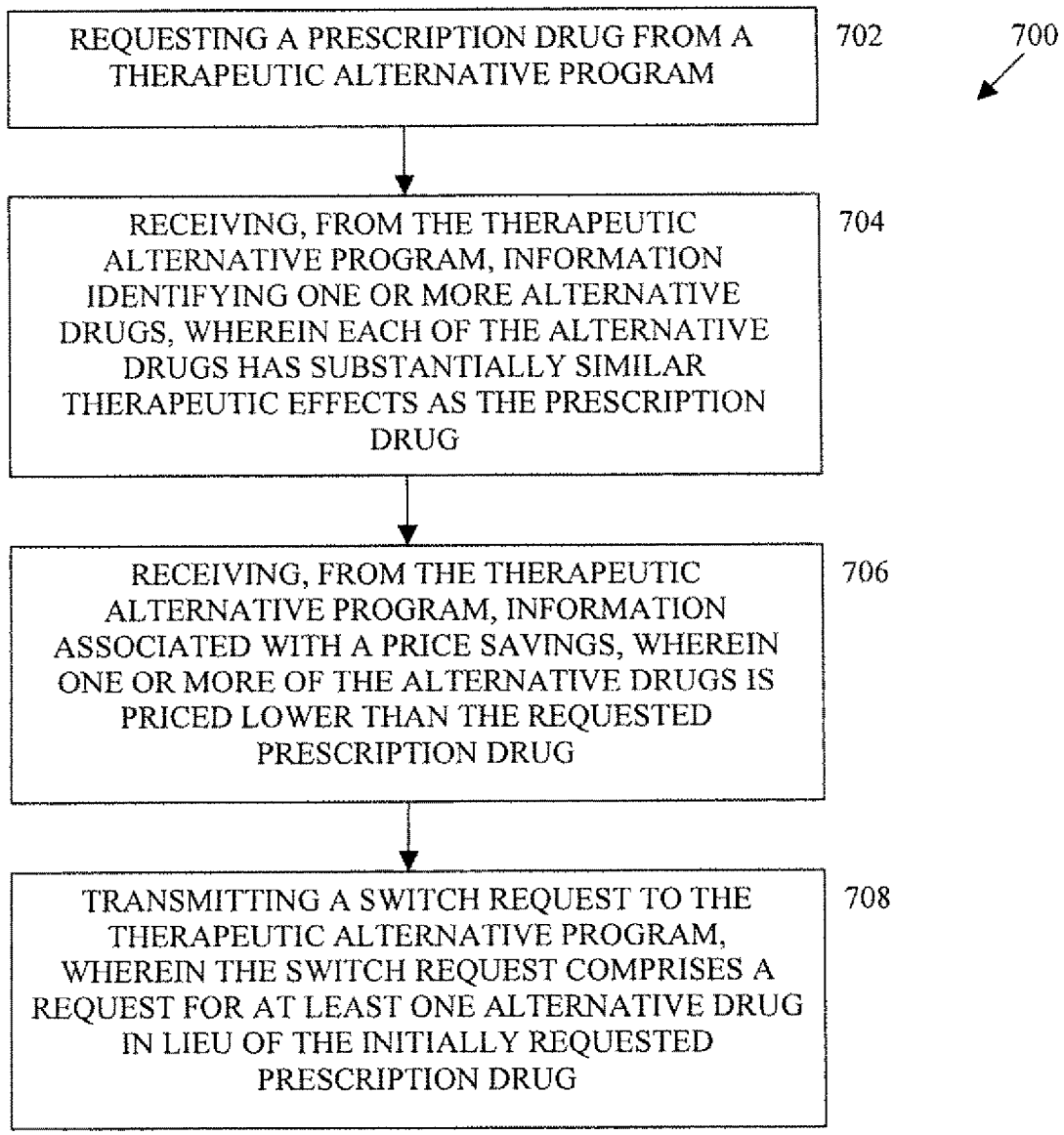

The example method 700 shown in FIG. 7 provides a method for obtaining an alternative to a prescription drug from a pharmacy. The method 700 can be implemented by a consumer, such as 424 of FIG. 4, in conjunction with a therapeutic alternative program system, such as 400.

The method 700 begins at block 702. In block 702, a prescription drug is requested from a therapeutic alternative program. For example, as shown in FIG. 4, a request for a prescription drug can be requested by a consumer, such as 424. The request can be received by a pharmacy 402 via an I/O interface 414 and/or client module 422. The processor 411 associated with the pharmacy 402 can receive the prescription drug request and process and/or transmit the request as needed.

Block 702 is followed by block 704, in which information identifying one or more alternative drugs is received from the therapeutic alternative program, wherein each of the alternative drugs has substantially similar therapeutic effects as the prescription drug. For example, as shown in FIG. 4, a processor 411 can transmit the request via the network to a switch provider 404. The processor 426 associated with the switch provider 404 can determine one or more alternative drugs that have substantially similar therapeutic effects as the requested prescription drug.

Block 704 is followed by block 706, in which information associated with a price savings is received from the therapeutic alternative program. For example, as shown in FIG. 4, the processor 426 associated with the switch provider 404 can calculate a price or cost savings by utilizing the difference in the alternative drug price and the price for a requested prescription drug. In one embodiment, the processor 426 can access a data storage device or database, such as 442, to obtain information associated with alternative drugs and the requested prescription drug.

In one embodiment, true prices for alternative drugs and the requested prescription drug can be calculated by using one or more discount rules. Examples of discount rules can include, but are not limited to, 100% co-pay plan rules for discounts, available manufacturer or provider rebates, coupons, vouchers, patient assistance, or similar price reduction methodologies associated with each. Based on the true prices, the processor 426 can calculate the cost savings.

In any instance, the processor 426 can transmit results via the network 410 to the pharmacy 402. The processor 411 associated with the pharmacy 402 can output the identity of the alternative drug and cost saving information via the I/O interface 414 and/or the client module 422. A consumer, such as 424, or other entity can review the identity of the alternative drug and cost savings information, including the name of a therapeutically equivalent drug, dosage, and cost savings, and the consumer 424 can make a decision regarding the selection of the alternative drug.

In one embodiment, an entity can be a pharmaceutical benefits manager, such as 408. For example, as shown in FIG. 4, the pharmacy 402 can transmit the identity of the alternative drug and cost savings information to the pharmaceutical benefits manager 408 for review. The processor 458 associated with the pharmaceutical benefits manager 408 can output the identity of the alternative drug and cost saving information via the I/O interface 462 and/or the host module 472. A person, such as 424, or other entity can review the identity of the alternative drug and cost savings information, and make a decision regarding the selection of the alternative drug.

Block 706 is followed by block 708, in which a switch request is transmitted to the therapeutic alternative program, wherein the switch request comprises a request for at least one alternative drug in lieu of the initially requested prescription drug. For example, as shown in FIG. 4, a consumer, such as 424, can input a switch request via the I/O interface 414 and/or the client module 422. The switch request, including a decision to switch from the prescription drug to the alternative drug, can be transmitted to the processor 411 for further processing.

In another embodiment, a switch request can be input via the I/O interface 462 and/or the host module 472 associated with the pharmaceutical benefits manager 408. The switch request, including a decision to switch from the prescription drug to the alternative drug, can be transmitted to the processor 458 for further processing.

The method 700 of FIG. 7 ends at block 708.

Figure 8:
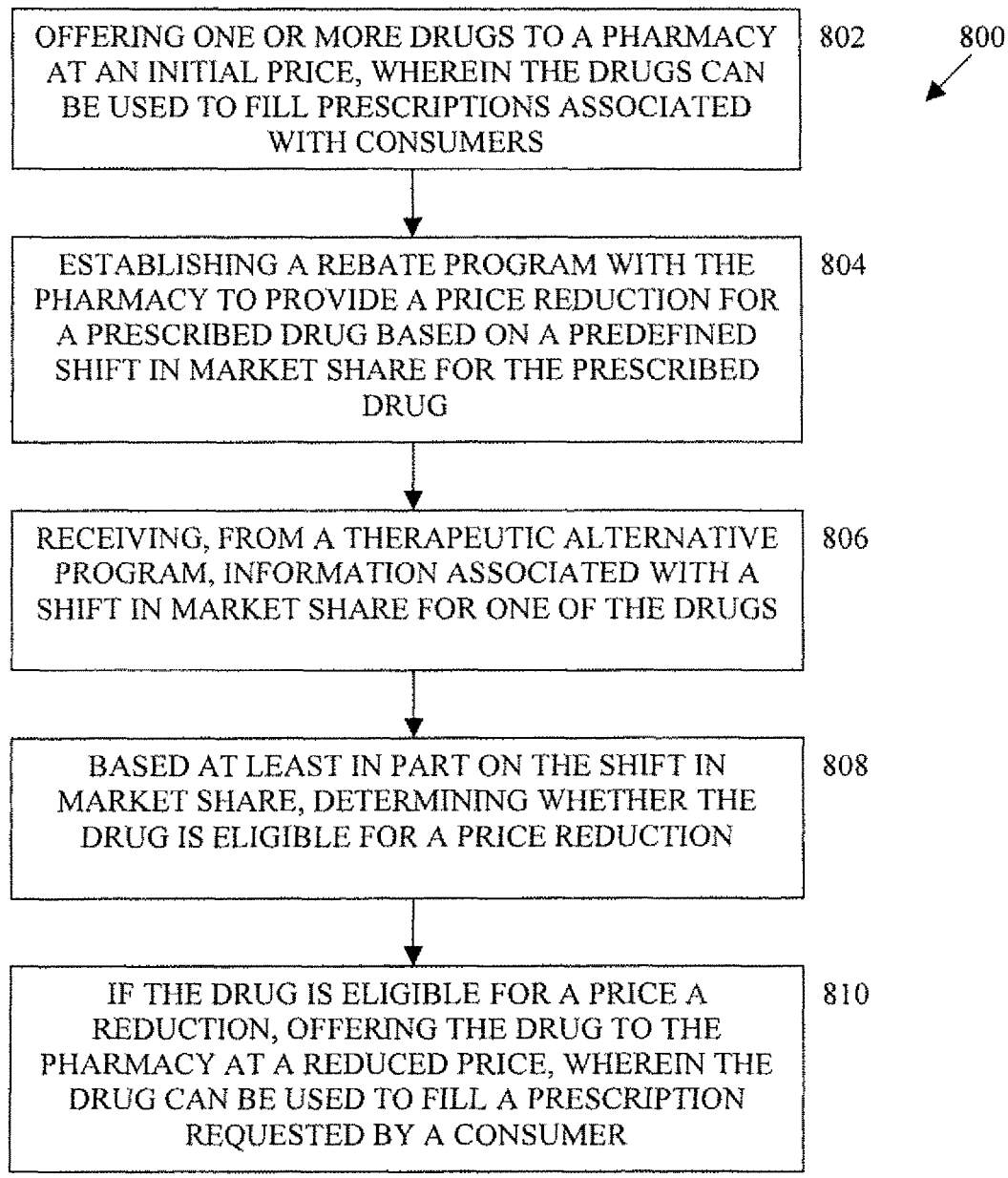

The example method 800 shown in FIG. 8 provides a method for facilitating a shift in drug market share. The method 800 can be implemented by a therapeutic alternative program system, such as 400 of FIG. 4.

The method 800 begins at block 802. In block 802, one or more drugs are offered to a pharmacy at an initial price, wherein the drugs can be used to fill prescriptions associated with consumers. For example, as shown in FIG. 4, a pharmaceutical manufacturer or provider 406 can provide or otherwise offer one or more drugs to a pharmacy 402 to fill prescriptions requested by consumers, such as 424.

Block 802 is followed by block 804, in which a rebate program is established with the pharmacy to provide a price reduction for a prescribed drug based on a predefined shift in market share. For example, as shown in FIG. 4, the pharmaceutical manufacturer or provider 406 can contractually agree with one or more pharmacies, such as 402, to provide price reductions for the drugs based on a predefined shift in market share. In one embodiment, one or more predefined discount rules can be implemented by and between a pharmaceutical manufacturer or provider 406 and pharmacy 402 to provide a price reduction for at least one drug based at least in part on a particular shift in market share for a particular drug or drugs.

Block 804 is followed by block 806, in which information associated with a shift in market share for one of the drugs is received from a therapeutic alternative program. For example, as shown in FIG. 4, after decision information or switch request information is received by the processor 411, the decision information, including a decision to switch from the prescription drug to the alternative drug, can be transmitted via the network 410 to a pharmaceutical manufacturer or provider 406 some or all of the decision information received from the consumer 424. In another embodiment, the processor 426 associated with the switch provider 404 can transmit via the network 410 to a pharmaceutical manufacturer or provider 406 some or all of the decision information received from the consumer 424. In some instances, the processor 411, 426 may capture all data elements necessary from various pharmacy participants and compile it into a format that will provide information concerning market share shifts attained for specific drug entities for which pharmaceutical manufacturers or providers 406 have contracted to provide volume rebates for such shifts.

Block 806 is followed by block 808, in which based at least in part on the shift in market share, a determination is made whether the drug is eligible for a price reduction. For example, as shown in FIG. 4, the processor 442 associated with pharmaceutical manufacturer or provider 406 can receive some or all of the decision information associated with the consumer, and the processor 442 can determine whether the drug is eligible for a price reduction. The processor 442 can use predefined volume amounts, contractually defined volume amounts, drug sales data, or any other criteria to determine if a particular drug is eligible for a price reduction. In other embodiments, other components, such as processors 411, 426, and 458 can similarly determine eligibility for a price reduction.

Block 808 is followed by block 810, in which if the drug is eligible for a rebate, the drug is offered to the pharmacy at a reduced price, wherein the drug can be used to fill a prescription requested by a consumer. For example, as shown in FIG. 4, if a particular drug is eligible for a rebate, the processor 442 can determine the appropriate rebate and transmit suitable pricing information via the network 410 to the pharmacy 402. In turn, the pharmacy 402 can provide the drug at the reduced price to consumers. In addition, the processor 442 can determine any rebate revenues for pharmacy participants in accordance with any contractual agreements, such as between a pharmacy 402 and a pharmaceutical manufacturer or provider 406. The processor 442 can provide suitable rebate information via the network 410 to the switch provider, such that the switch provider 404 can determine or otherwise apportion any rebate revenues payable to a pharmacy 402 or other pharmacy participants.

The method 800 of FIG. 8 ends at block 810.

Figure 9:
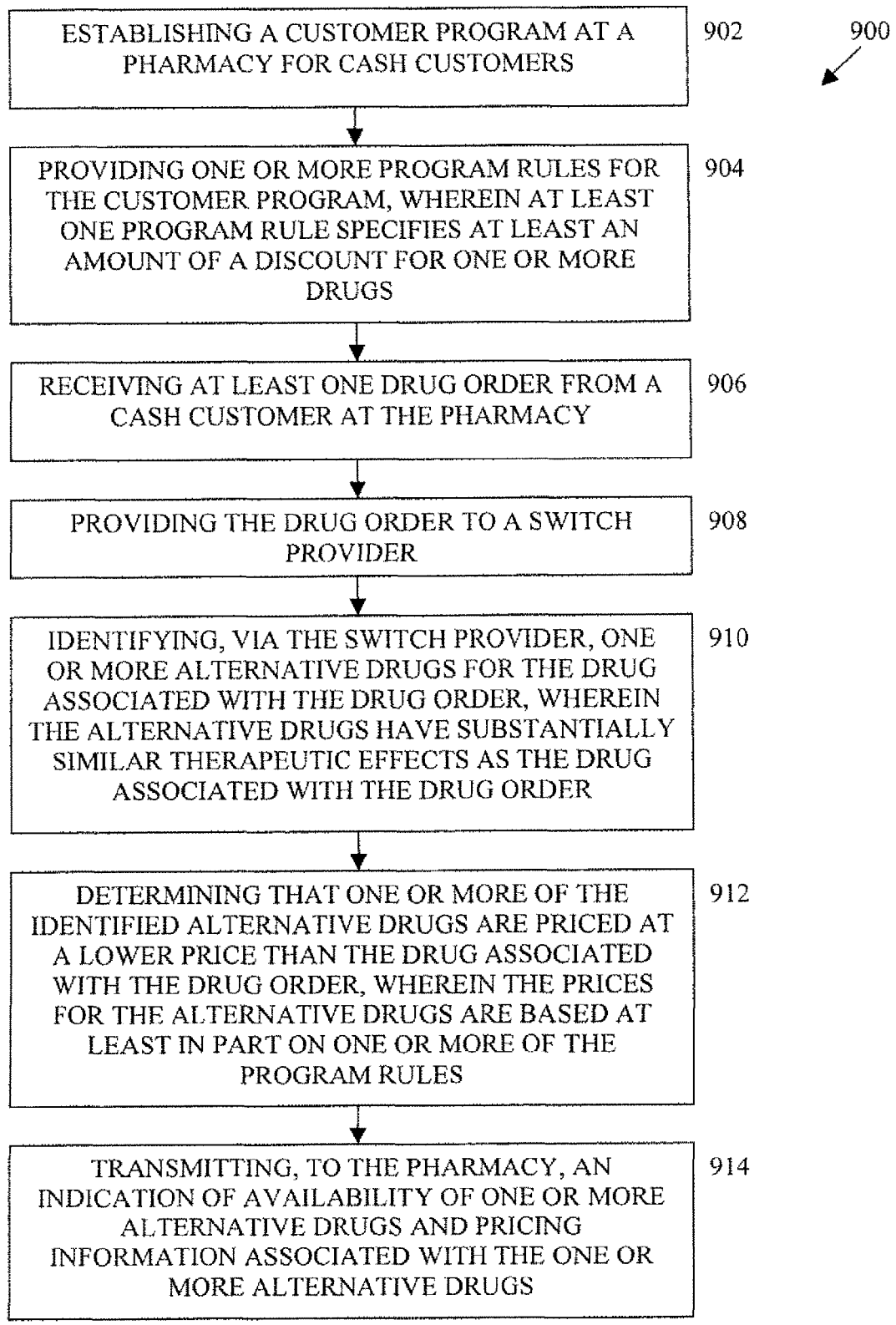

The example method 900 shown in FIG. 9 provides a method for enhancing revenues of a pharmacy. The method 900 can be implemented by a therapeutic alternative program system, such as 400 of FIG. 4.

The method 900 begins at block 902. In block 902, a customer program is established at a pharmacy for cash customers. For example, as shown in FIG. 4, a pharmacy 402 and/or a pharmaceutical manufacturer or provider 406 can provide or otherwise offer a customer program to consumers, such as 424, who purchase one or more drugs with cash to fill prescriptions.

Block 902 is followed by block 904, in which one or more program rules can be provided for the customer program, wherein at least one program rule specifies at least an amount of a discount for one or more drugs. For example, as shown in FIG. 4, the pharmaceutical manufacturer or provider 406 can contractually agree with one or more pharmacies, such as 402, to provide price reductions for the drugs based on a predefined shift in market share. In one embodiment, one or more predefined discount rules can be implemented by and between a pharmaceutical manufacturer or provider 406 and pharmacy 402 to provide a price reduction for at least one drug based at least in part on a particular shift in market share for a particular drug or drugs.

Block 904 is followed by block 906, in which at least one drug order is received from a cash customer at the pharmacy. For example, as shown in FIG. 4, a request for a prescription drug can be requested by a consumer, such as 424. The request can be received by a pharmacy 402 via an I/O interface 414 and/or client module 422. The processor 411 associated with the pharmacy 402 can receive the prescription drug request and process and/or transmit the request as needed.

Block 906 is followed to block 908, in which the drug order is provided to a switch provider. For example, as shown in FIG. 4, a processor 411 associated with the pharmacy 402 can transmit the information via the network to a switch provider 404.

Block 908 is followed by block 910, in which one or more alternative drugs for the drug associated with the drug order is identified, wherein the alternative drugs have substantially similar therapeutic effects as the drug associated with the drug order. For example, as shown in FIG. 4, the processor 426 associated with the switch provider 404 can determine one or more alternative drugs that have a similar therapeutic effects as the drug associated with the drug order. In one embodiment, the processor 426 can access a data storage device or database, such as 442, to obtain information associated with alternative drugs and the prescription drug.

Block 910 is followed by block 912, in which one or more of the identified alternative drugs are determined to be priced at a lower price than the drug associated with the drug order, wherein the prices for the alternative drugs are based at least in part on one or more of the program rules. For example, as shown in FIG. 4, the processor 426 associated with the switch provider 404 can determine and compare the prices for the alternative drugs and the price for a requested prescription drug. In one embodiment, the processor 426 can access a data storage device or database, such as 442, to obtain information associated with alternative drugs and the prescription drug.

In one embodiment, true prices for alternative drugs and a requested prescription drug can be calculated by using one or more discount rules. Examples of discount rules can include, but are not limited to, 100% co-pay plan rules for discounts, available manufacturer or provider rebates, coupons, vouchers, patient assistance, or similar price reduction methodologies associated with each.

Block 912 is followed by block 914, in which an indication of availability of one or more alternative drugs and pricing information associated with the one or more alternative drugs is transmitted to the pharmacy. For example, as shown in FIG. 4, the processor 426 can transmit results via the network 410 to the pharmacy 402. The processor 411 associated with the pharmacy 402 can output the identity of the alternative drug and pricing information via the I/O interface 414 and/or the client module 422. A consumer, such as 424, or other entity can review the identity of the alternative drug and pricing information, including the name of a therapeutically equivalent drug, dosage, and cost savings, and the consumer 424 can make a decision regarding the selection of the alternative drug.

The method 900 of FIG. 9 ends at block 914.

The example elements and steps of FIGS. 5-9 are shown by way of example, and other process embodiments can have fewer or greater numbers of elements or steps, and such elements or steps can be arranged in alternative configurations in accordance with other embodiments of the invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for facilitating a shift in drug market share, comprising:
    offering, by at least one computer processor, one or more drugs to a pharmacy at an initial price, wherein the drugs can be used to fill prescriptions associated with consumers;
    establishing, by at least one computer processor, a rebate program with the pharmacy to provide a price reduction for a prescribed drug based on a shift in market share for the prescribed drug;
    receiving, by at least one computer processor, from a therapeutic alternative program, information associated with a shift in market share for the prescribed drug;
    prior to providing a price reduction for the prescribed drug based at least in part on the shift in market share, determining, by at least one computer processor, whether the drug is eligible for a price reduction; and
    after a determination is made that the drug is eligible for a price reduction, offering, by at least one computer processor, the drug to the pharmacy at a reduced price, wherein the drug can be used to fill a prescription requested by a consumer.

* * * * *